United States Patent [19]

Husted

[11] Patent Number: 4,909,781

[45] Date of Patent: Mar. 20, 1990

[54] CATHETER WITH FLEXIBLE CUTTER

[76] Inventor: Royce H. Husted, 711 Lakeside Dr., Wheaton, Ill. 60187

[21] Appl. No.: 384,062

[22] Filed: Jul. 19, 1989

Related U.S. Application Data

[63] Continuation of Ser. No. 179,069, Apr. 8, 1988, abandoned.

[51] Int. Cl.[4] .............................................. A61B 17/32
[52] U.S. Cl. ....................................... 604/22; 606/194; 606/159
[58] Field of Search .................... 128/305, 310, 303 R, 128/753, 754, 755; 604/22

[56] References Cited

U.S. PATENT DOCUMENTS

| | | | |
|---|---|---|---|
| 3,749,085 | 7/1973 | Willson et al. ................... | 128/305 X |
| 4,653,496 | 3/1987 | Bundy et al. .......................... | 128/753 |
| 4,772,258 | 9/1988 | Marangoni et al. .................. | 604/22 |
| 4,819,634 | 4/1989 | Shiber ................................. | 128/305 |

FOREIGN PATENT DOCUMENTS 401360  2/1974  U.S.S.R. ............................ 128/754

*Primary Examiner*—Michael H. Thaler
*Attorney, Agent, or Firm*—Nicholas A. Camasto

[57] ABSTRACT

A flexible catheter for opening obstructions in blood vessels comprises a coil spring rotatably mounted in the end of a hollow tube. The spring is driven off center by a flexible wire drive shaft that is an extension of the coil spring. The end turn of the coil spring forms a cutting edge. A thin, flexible wire guide is affixed to the outside of the hollow tube adjacent to the coil spring and extends in front of the cutting edge. The wire guide has a free end that passes back into the coil spring and hollow tube. The wire guide follows the orientation of the blood vessel and guides the coil spring.

10 Claims, 2 Drawing Sheets

CATHETER WITH FLEXIBLE CUTTER

This application is a continuation of application Ser. No. 07/179,069, filed 4/8/88, now abandoned.

CROSS-REFERENCE TO RELATED PATENT APPLICATION

The catheter of the present application is related to that disclosed in copending application Ser. No. 77,981, filed 7/27/87, entitled CATHETER WITH A ROTARY BLADE now U.S. Pat. No. 4,754,755, dated 7/5/88.

BACKGROUND OF THE INVENTION AND PRIOR ART

The present invention is useful for opening obstructions in blood vessels, such as human arteries. Much attention has been devoted to the development of techniques and apparatus for opening arterial obstructions to replace the dangerous, costly and rarely permanent bypass procedure. The copending application describes a catheter with a unique cutting tip that provides a substantially unobstructed passageway into and through the catheter for cut material due to its shape and drive arrangement. In that application, a thin-walled cylindrical cutter is driven by means of a thin, flexible wire attached to the cutter wall. The resulting off center drive arrangement enables free flow of cut material through the cutter and into the hollow catheter tube. Suction may be applied to the catheter to assist in drawing the cut material into the tube. It will be appreciated that the catheter tube of that invention and of the present invention may be used as the inner of two concentric tubes wherein a saline solution, or the like, may be introduced to the site of the obstruction through the outer tube and removed via the inner tube.

When dealing with large blood vessels, such as the femoral artery, relatively rigid catheter structures may be utilized with some degree of success. However, when dealing with very small blood vessels or with vessels that include relatively sharp bends or turns, the catheter must be extremely flexible. In general, a thin guide wire is positioned by the surgeon next to an obstruction in a blood vessel and a catheter tube introduced over the guide wire. The guide wire may be removed before commencing blockage opening procedures. Various well-known fluoroscopy techniques may be utilized for assisting the positioning of the guide wire, the guiding of the catheter to the site of the obstruction and the operation of the obstruction opening device.

In accordance with one aspect of the invention, the need for a separate guide wire is eliminated. In accordance with another aspect of the invention, the cutter tip itself is flexible to permit it to follow the orientation of the obstructed vessel and to negotiate relatively sharp turns therein.

OBJECTS OF THE INVENTION

It is a principal object of the invention to provide an improved catheter.

Another object of the invention is to provide a self-guiding catheter.

A further object of the invention is to provide a catheter that more readily conforms to bends and turns in blood vessels.

A still further object of the invention is to provide a catheter that is much safer in use.

A feature of the invention is its unitary design of flexible off center drive shaft, flexible cutter body and cutting edge.

BRIEF DESCRIPTION OF THE DRAWINGS

These and other objects and advantages of the invention will be apparent upon reading the following description in conjunction with the drawings, in which.

DESCRIPTION OF THE PREFERRED EMBODIMENT

Figure 1:
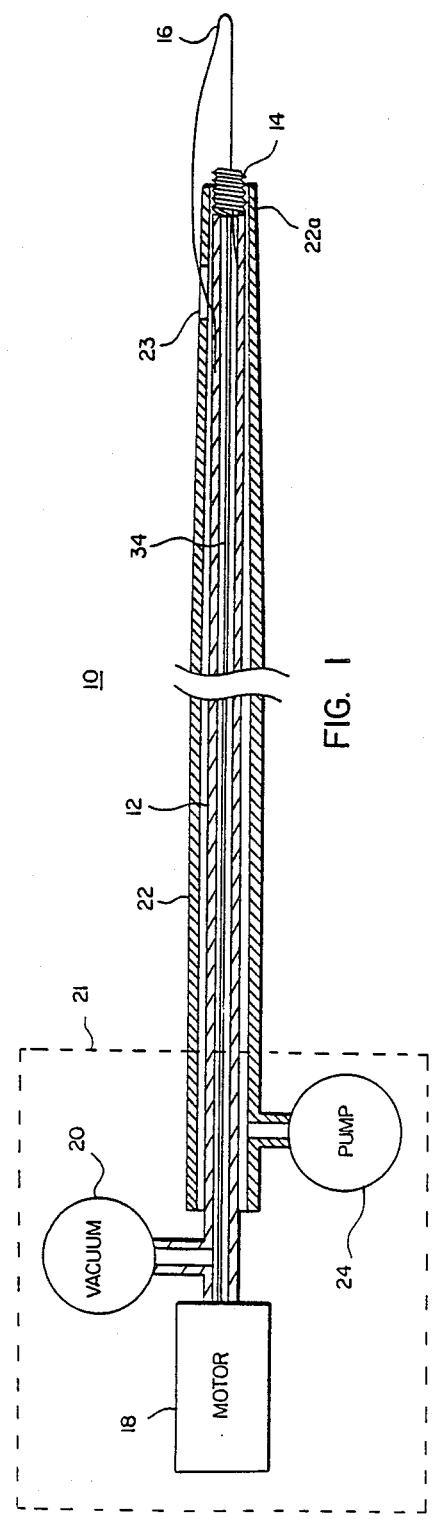
FIG. 1 is a simplified representation of a catheter constructed in accordance with one form of the invention.

Referring to FIG. 1, a catheter generally designated by reference numeral 10 includes a small diameter inner flexible tube 12 terminating in a novel hollow flexible coil spring cutter 14 and a fine guide wire 16. Hollow cutter 14 is rotatably driven by a thin, flexible wire drive shaft 34 that extends the length of tube 12 and is coupled to a motor 18. In accordance with the invention in the copending application, hollow cutter 14 is driven in an off center manner by drive shaft 34. A source of vacuum 20 is connected to one end of tube 12 to assist cut material (not shown) being drawn into the other end of catheter 12 through hollow cutter 14. In one embodiment of the invention, a similarly configured outer hollow tube 22, substantially coextensive with tube 12, may be used in conjunction with a pump 24 for injecting a saline solution or the like through the annular space between concentric tubes 22 and 12 to the side of the obstruction adjacent cutter 14. The end of the outer hollow tube 22 may also serve as a bushing, as at 22a, which holds flexible coil spring cutter 14 in axial confinement. Guide wire 16 is very thin and flexible and is used by the surgeon to guide the catheter through a blood vessel and to the site of the obstruction that is to be opened or removed. A rounded end 16a helps guide wire 16 to follow the path of the blood vessel. It will be appreciated that the motor, pump and vacuum source, enclosed by dashed line box 21 are schematically illustrated only. A slot 23, in outer tube 22, enables tube 22 to be axially moved relative to tube 12, as will be explained.

Figure 2:
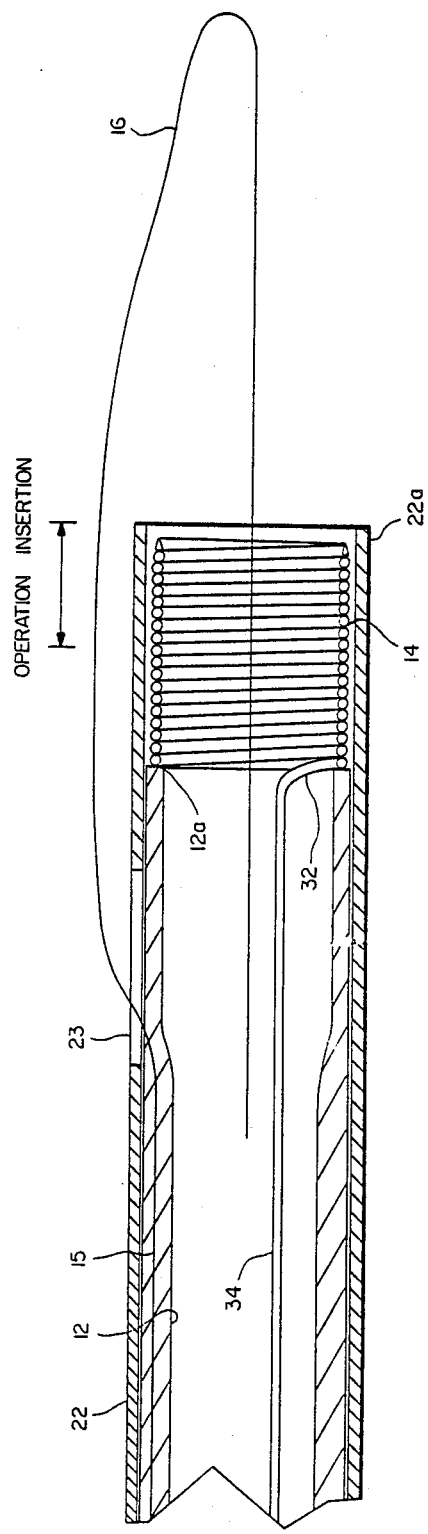
FIG. 2 is an enlarged view of the unitary flexible cutter and guide wire of the catheter of FIG. 1.

In FIG. 2, tube 22 is shown in its forwardmost position, as it would be while inserting and guiding the catheter into position adjacent to an obstruction. When tube 22 is axially moved to the forward Insertion position, it completely covers cutter 14, and when it is retracted to the Operation position, it is pulled back relative to tube 12 to expose a substantial portion of flexible cutter 14. Slot 23 in tube 22 permits movement between the Insertion and Operation positions without disturbing guide wire 16.

The end portion of tube 12 may have a thinner wall to promote flexibility and may have a slightly greater diameter than the diameter of coil spring cutter 14. This provides a shoulder 12a for the cutter to bear against during its rotation. End 15 of guide wire 16 is embedded in the wall of tube 12 and rigidly secured thereto. This configuration is preferred when two concentric tubes are desired or needed for the catheter.

Figure 3:
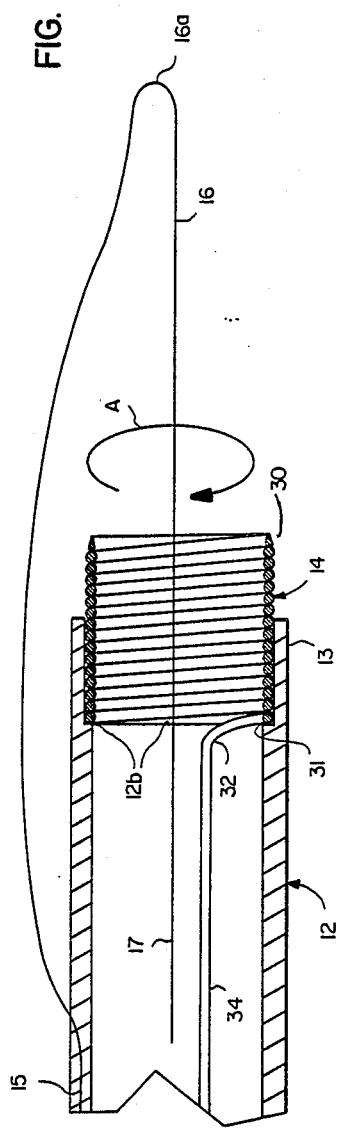
FIG. 3 is an enlarged cutaway portion of a unitary flexible cutter and guide wire constructed in accordance with another form of the invention.

In FIG. 3, another embodiment using the novel flexible cutter 14 is disclosed. Tube 12 is seen to have a larger diameter cross section near its end 13 forming a lip or shoulder 12b. The inner surface of end 13 in this embodiment provides a bearing for cutter 14 to rotate in, generally in the direction of the circular arrow A. Guide wire 16 is formed of a fine piano wire or the like and includes a sharp bend to form a rounded tip 16a and has one end 15 securely embedded in the wall of tube 12 by any suitable means, such as by gluing, and its other end 17 extends freely through the central opening of coil spring cutter 14 and terminates inside tube 12. The outer end turn 30 of coil spring cutter 14 is preferably shaped to form a cutting edge 14a and the end turn 31 adjacent shoulder 12b is bent at 32 at substantially a right angle, and extends parallel to the axis of the cutter 14 through the length of tube 12, where it is coupled to drive motor 18 via drive shaft 34. This embodiment of the invention does not use an outer tube and inner shoulder 12b in end 13 functions as a type of thrust bearing to help rotatably confine flexible cutter 14. This particular construction should not be considered limiting of the invention, however. Bend 32 should be made in such a way so as to maintain a substantially open passenger through hollow cutter 14 for ingress of cut material. It will also be apparent that the cutting edge 14a on end turn 30 of the coil spring cutter may be formed in any of a variety of ways, including having the taper oppositely extending to that shown so that an outward flare is imparted to the open end of cutter 14. As indicated, the direction of rotation (arrow A) of cutter 14 is such that end turn 30 tends to remain closely coupled to its adjacent coil spring turn. It will also be appreciated that, rather than using the end turn of the coil spring as the cutting edge, a separate annular cutting element may be affixed to the end turn of the spring by any suitable means. It is also contemplated that end turn 30 may be flattened to present a cross section that is more readily adapted and shaped into a cutting edge. Any of such constructions would not materially affect the flexibility of the body of cutter 14, which is a key aspect of the invention.

It will, of course, be apparent to those skilled in the art that the preferred one-piece, off center drive shaft and open, flexible cutter design lends itself to extreme miniaturization. Since even a 20% opening in a blocked vessel may provide sufficient blood flow, this miniaturization capability makes the inventive design very attractive.

Figure 4:
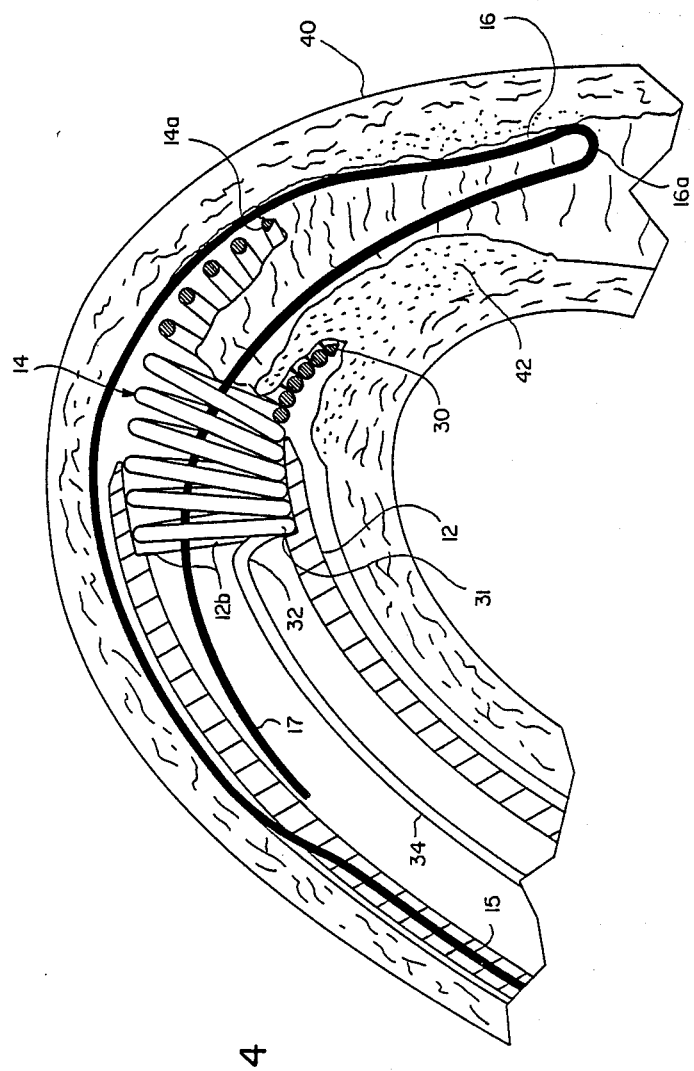
FIG. 4 is a partial cutaway section depicting use of the catheter of FIG. 3 to remove obstructions in a curved portion of a blood vessel.

In FIG. 4, the flexible coil spring cutter 14, tube 12 and guide wire 16 of FIG. 3 are shown in position in a blood vessel 40 that the partial obstruction or blockage 42. Guide wire 16 and rounded tip 16a enable the tube 12 to follow the bends of the blood vessel 40 and to be positioned with end turn 14a of cutter 14 adjacent to the obstruction 42. As mentioned, guide wire 16 is very flexible and readily conforms to the bends and turns in the blood vessel 40. As the guide wire 16 bends, it forces flexible cutter 14 to follow. Also as mentioned, the surgeon constantly monitors the position and orientation of the catheter via a fluoroscope or the like while it is being inserted and adjusts its orientation to keep the outside portion of guide wire 16 adjacent to the large radius side of a turn in the vessel. Throughout its insertion and operation, cutter 14 is confined by guide wire 16 with precludes the possibility of inadvertently puncturing or cutting through the wall of vessel 40. As cutter 14 is rotated, via the off center rotational drive force applied through drive shaft 34, free end 17 of guide wire 16 will be nudged out of the way every revolution since guide wire 16 does not rotate.

Those skilled in the art will readily recognize that the cutter 14 need not be confined within the end of tube 12. Rather, operation of the coil spring cutter of the invention completely outside of the catheter tube is envisioned, especially when used with a guide wire, and when so configured, the vessel itself serves as the annular confinement for the rotary coil spring cutter.

It is recognized that numerous changes and modifications in the described embodiment of the invention will be apparent to those skilled in the art without departing from its true spirit and scope. The invention is to be limited only as defined in the claims.

What is claimed is:

1. A catheter for opening obstructions in blood vessels comprising:
   a thin, flexible, cylindrical tube adapted for insertion in a vessel adjacent to an obstruction;
   an annular cutter having a forwardly disposed cutting edge positioned at one end of said cylindrical tube and adapted for rotation therein;
   said annular cutter having a flexible coil spring body;
   a loop of thin wire extending forwardly of said cutting edge outside said coil spring body and having one end fixed to said cylindrical tube for guiding and bending the flexible coil spring body of said annular cutter to follow the orientation of said vessel; and
   wire means for imparting an off center rotational driving force to said body.

2. The catheter of claim 1 wherein said coil spring body has an end turn that forms said forwardly disposed cutting edge.

3. The catheter of claim 2 wherein said wire means comprise an extension of said coil spring body.

4. The catheter of claim 3 wherein said annular cutter is positioned at least partially within said one end of said cylindrical tube.

5. The catheter of claim 4, further including means for providing suction in said cylindrical tube for assisting entry of material cut from said obstruction into said annular cutter and cylindrical tube.

6. The catheter of claim 5, further including a concentric outer flexible cylindrical tube that is movable axially to cover and expose said cutting edge.

7. A catheter for opening obstructions in blood vessels comprising:
   a thin, flexible, cylindrical tube adapted for insertion in a vessel adjacent to an obstruction;
   an annular cutter positioned at one end of said cylindrical tube and adapted for rotation therein;
   said annular cutter having a flexible coil spring body and terminating in a cutting edge;
   guide means comprising a loop of thin wire extending forwardly of said cutting edge outside said coil spring body and having one end fixed to said cylindrical tube and the other end freely extending through said annular cutter for guiding and bending the flexible coil spring body of said annular cutter to follow the orientation of said vessel; and
   wire means for imparting an off center rotational driving force to said body.

8. A catheter for use in clearing an obstruction in a blood vessel comprising:
   a thin, flexible, hollow tube adapted to be positioned in a vessel with one end adjacent to an obstruction therein;
   a hollow coil spring rotatably movable in said one end of said hollow tube and having a forwardly disposed annular cutting edge extending outside said one end of said hollow tube;
   a thin, flexible wire extension of said coil spring extending within said tube for imparting a rotational drive force to said coil spring; and
   a thin, flexible wire guide extending forwardly of said cutter and having one end affixed to the outside of said hollow tube and a free end extending into said coil spring for following the course of said vessel and for forcing said coil spring to deflect in the direction of said course.

9. The catheter of claim 8, further including means for providing suction in said hollow tube for assisting movement of material cut from said obstruction into said coil spring and said hollow tube.

10. The catheter of claim 9, further including a concentric outer flexible cylindrical tube that is movable axially to cover and expose said cutting edge.

* * * * *

UNITED STATES PATENT AND TRADEMARK OFFICE
CERTIFICATE OF CORRECTION

PATENT NO. : 4,909,781

DATED : March 20, 1990

INVENTOR(S) : Royce H. Husted

It is certified that error appears in the above-identified patent and that said Letters Patent is hereby corrected as shown below:

Column 3, line 29, delete "passenger", insert --passageway--;

line 56, delete "the", insert --has a--;

Column 4, line 2, delete "with", insert --which--.

Signed and Sealed this

Third Day of December, 1991

*Attest:*

HARRY F. MANBECK, JR.

*Attesting Officer*      *Commissioner of Patents and Trademarks*